United States Patent [19]

Lin et al.

[11] Patent Number: 4,645,503
[45] Date of Patent: Feb. 24, 1987

[54] MOLDABLE BONE-IMPLANT MATERIAL

[75] Inventors: Steve T. Lin, Hayward; Seshadri Conjeevaram, Stockton; Don J. Henderson, Danville, all of Calif.

[73] Assignee: Orthomatrix Inc., Dublin, Calif.

[21] Appl. No.: 769,940

[22] Filed: Aug. 27, 1985

[51] Int. Cl.$^4$ .............................................. A61F 2/28
[52] U.S. Cl. ..................................................... 623/16
[58] Field of Search ................... 623/16; 433/173, 121; 128/334 R

[56] References Cited

U.S. PATENT DOCUMENTS

| | | | |
|---|---|---|---|
| 4,024,639 | 5/1977 | Weiss | 433/173 |
| 4,186,448 | 2/1980 | Brekke | 623/16 |
| 4,200,939 | 5/1980 | Oser | 623/16 |
| 4,222,128 | 9/1980 | Tomonaga | 623/16 |
| 4,329,743 | 5/1982 | Alexander et al. | |

OTHER PUBLICATIONS

Kulkarni et al., *J. Biomed. Mater. Res.*, vol. 5, pp. 169-181, (1971).
Getter et al., *J. Oral Surgery*, vol. 30, pp. 344-348, May 1972.

*Primary Examiner*—Gregory E. McNeill
*Attorney, Agent, or Firm*—Ciotti & Murashige

[57] ABSTRACT

A moldable bone-implant material containing between about 65%–95% hard filler particles and a binder composed of between about 35%–5% of a biocompatible, biodegradable, thermoplastic polymer which has fluidic flow properties at or below about 60° C. One preferred binder is polylactic acid having a molecular weight between about 400 and 5,000 daltons, and a preferred hard filler is hydroxylapatite. In use, the material is warmed to a temperature which allows molding, and the bone site is filled with the moldable material, which then forms a contour-fitting, semi-rigid implant. The implant retains its contour fit and acquires a rigid final state as the binder in the implant is gradually biodegraded and replaced through tissue ingrowth from the surrounding bone site.

16 Claims, No Drawings

MOLDABLE BONE-IMPLANT MATERIAL

FIELD OF THE INVENTION

The present invention relates to a moldable bone-implant material formed of hard bone graft filler particles bound together with a moldable biodegradable polymer.

BACKGROUND OF THE INVENTION

Bone implants are used for bone reconstructive surgery and repair where bone loss or traumatic damage has occurred. In addition to the usual function of strengthening and filling in a repaired bone area, implants can also act to transmit forces to the surrounding bone area, to preserve the vitality of the bone. As an example of the latter function, bone implants are commonly placed in tooth-extraction sites, to help preserve the underlying alveolar bone by providing for continued force on the bone during chewing.

The most proven and accepted synthetic material for bone reconstruction and repair is hydroxylapatite. This material has outstanding biocompatibility, due to its similarity to bone in composition and crystalline structure. The most important property of hydroxylapatite is its ability to bond directly to bone and act as a scaffold for ingrowth of surrounding bone tissue into the matrix of the particles. The tissue ingrowth acts to stabilize the implant on the surrounding bone and, where the implant is formed of hydroxylapatite particles, forms a tissue matrix which helps maintain the integrity of the implant.

One type of hydroxylapatite implant which has been used heretofore is a rigid implant which is intended to be machined by the surgeon or dentist to fit the implant site. The implant may be formed of a solid block of hydroxylapatite or a porous, continuous-phase hydroxylapatite block impregnated with a polymer resin to improve the strength and/or bone compatibility of the block, as disclosed, for example, in U.S. Pat. No. 4,222,128. Alternatively, solid hydroxylapatite blocks have been formed by binding hydroxylapatite particles with a permanent, rigidifying polymer material. Implants of this type suffer from a number of disadvantages. The process of determining the shape of the bone site and fashioning the implant to fit the site is time consuming and complicates the surgery. The implant rarely is ideally shaped and therefore may work loose in the site before tissue ingrowth can occur. Such implants require suturing soft tissue to hold them in place, and may require protecting the site against movement for an extended post-operative period. Also, the implant cannot be fashioned to take advantage of undercut surfaces at the bone site which otherwise might contribute to anchoring the implant. Up to 90% of such implants have been reported to work loose within the first year of implantation.

Implants formed of loose non-bonded hydroxylapatite particles are also well known in the prior art. In preparing an implant of this type, the particles are wet with saline or the patient's blood to give the particles some cohesion and make them manageable during the implant procedure. The loose mass of particle material is placed in the bone site, where it can adopt to the contours of the surrounding support tissue. After implantation, the particle mass is ingrown with hard or soft tissue which stabilizes the mass of particles, typically in a period of a few days to weeks. The implant can thus acquire a rigid contoured fit, and can also conform to undercut regions in the site to provide increased anchorage.

Despite the advantages of loose-particle implants, a number of problems have been encountered. Loose particles are generally difficult to deliver to the site in a convenient manner, and paraphernalia, such as mixing dishes, applicator funnels, suction devices, and the like, may be required. The particle mass has little cohesive strength and very often loses its shape before the mass is stabilized by tissue ingrowth. For example, particles used for rebuilding the alveolar ridge often exhibit ridge flattening and hence a loss of ridge height before the implant particles can be stabilized by tissue ingrowth. The loose cohesion of the particle mass also allows particles to migrate away from the implant site before tissue ingrowth is complete, and this can result in implant failure and exfoliation of particles into the patient's mouth in the case of oral implants.

SUMMARY OF THE INVENTION

It is a general object of the invention to provide a bone-implant material which substantially overcomes problems associated with existing solid rigid-block and loose-particle types of implant materials.

A more specific object of the invention is to provide such material which overcomes the disadvantages of loose-particle implant placement, including loss of implant material and shape, while maintaining the contour-fit and exceptional bone-like and biological ingrowth characteristics of particulate hydroxylapatite.

A related object of the invention is to provide such a material which is readily molded to fit the contours and undercut regions of a bone implant site.

Still another object of the invention is to provide a method using such material for filling a bone site with a rigid, contour-fitting, hydroxylapatite implant.

The invention includes a bone implant material which can be readily molded at a selected temperature at or below about 60° C. The material is formed as a cohesive mixture of hard filler particles and a binder composed of a biocompatible, biodegradable thermoplastic polymer having fluid-flow properties at the selected temperature at or below about 60° C.

The degree of plasticity or moldability of the material, at a selected temperature, varies according to the chemical structure and molecular weight composition of the binder, allowing the material to be formulated to have desired moldability properties at a selected temperature. The polymer molecular weight is also compatible with a polymer degradation rate which allows gradual polymer replacement in the material by in situ tissue ingrowth over a several-day to several-week period. In a preferred embodiment, the polymer includes polylactic acid having a molecular weight between about 400 and 5,000 daltons.

The binder preferably constitutes no more than about one-third of the total solid volume of the material, leaving void space in the material which can accommodate tissue ingrowth. The minimum amount of binder is that necessary to give easy formability and provide sufficient particle cohesion and shape retention during the period of tissue ingrowth.

In the method of the invention, the moldable bone-implant material is moldable at ambient, or room temperature or heated to a suitable molding temperature, and the implant bone site is filled with the moldable material to form a contour-fitting implant in the site. The material may be dispensed from a syringe, tube-type dispenser, dish, or in soft block or roll form. The mold-in-place implant substantially retains its contour-fitting shape, during the several-day to several-week period when the binder is gradually degraded and replaced by tissue ingrowth from the surrounding bone site, to rigidify the implant.

These and other objects and features of the invention will become more fully apparent from the following detailed description of the invention.

DETAILED DESCRIPTION OF THE INVENTION

1. Preparing the Implant Material

The bone-implant material of the invention is prepared by mixing hard bone-graft filler particles with a biocompatible thermoplastic binder which is flowable at or below a selected temperature of about 60° C. The resulting material is moldable at the selected temperature, allowing the material to be applied to a bone site in a contour-fitting manner (as described in the next section).

Any hard biocompatible filler particles, including autogenous bone chips, can be used in this invention. However hydroxylapatite is the preferred filler for its permanance and biological profile. Tricalcium phosphate and glass granules may also be used alone or in combination with hydroxylapatite, particularly if some degree of resorption is desired in the filler.

Hydroxylapatite particles are preferably the type of dry free-flowing hydroxylapatite particles supplied for use in forming wetted, loose-mass implants, and can be obtained commercially from Orthomatrix Corporation (Dublin, CA) or Calcitek (San Diego, CA). Particle sizes of between about 250 and 2000 microns are preferred, smaller particles showing increased difficulty in allowing tissue ingrowth and larger particles requiring increased quantities of binder for ease of application.

The thermoplastic polymeric binder used in forming the bone graft material is selected for three important properties: (a) susceptibility to rapid biodegradation, to allow for gradual binder replacement by tissue during tissue ingrowth, without retarding ingrowth; (b) flowability or fluid-flow properties, which allow the material to be molded during implantation, to achieve a contour fit at the bone site; and (c) biocompatibility, that is, the binder should not provoke a serious inflammatory or other tissue-rejection response, at least within the several-week period when tissue ingrowth replacement is occurring.

For most biodegradable polymers of interest, biodegradation will involve hydrolytic cleavage by enzymes which are specific for the polymer subunit linkage. Preferred polymers are those which are degraded to metabolites which are normal to the body. Examples of such polymers include polylactic acid (PLA), polyglycolic acid, polyhydroxybutyric acid, polymalic acid, polyglutamic acid, and polylactone. Synthetic thermoplastic polymers of this type can be made quite uniform and consistent. The polymers may be either homopolymers or mixed polymers, such as copolymers.

The thermoplastic nature of the polymeric binder is advantageous in the present invention for several reasons. The polymer may be hand formed as a relatively low-viscosity mixture when warmed to an elevated temperature, and then assume a relatively high viscosity, more rigid shape when cooled to body temperature. Also, the thermoplastic nature of the binder allows the plasticity of the material to be increased readily just prior to implantation, for ease of implanting the material or preforming shapes. Finally, the binder fluid-flow properties can be molecular weight controlled to provide plasticity only above a certain temperature, e.g., 40° C., so that the material, once implanted in a bone site, assumes a more rigid, shape-retaining condition.

The binder preferably ranges in fluid-flow properties (flowability) between a highly viscous fluid and a putty-like semi-solid, at the selected temperature. With too low a binder viscosity, the implant material suffers the same problems seen in loose-particle implants: poor shape retention, once molded, and poor cohesiveness, leading to exfoliation of particles before or during the tissue ingrowth period.

According to one finding of the invention, the desired fluid-flow properties can be obtained by preparing the thermoplastic polymer under controlled conditions which result in polymer molecular weights which are within a defined size region, generally at the low end of molecular polymer sizes. The reaction conditions which produce optimal polymer sizes can be determined by monitoring the fluid-flow state of a polymer mix at several time points during the course of polymer synthesis. Typically polymer synthesis, as in the case of PLA, is carried out at a temperature well above 60° C., where the polymer mix is quite fluidic. To monitor flow properties, therefore, the polymer mix must first be cooled to the selected temperature where viscosity of the polymer may be determined. The molecular weight range of the polymers may be measures by conventional methods, such as get permeation chromatography. Studies reported below indicate desired flow properties are achieved with polylactic acid polymers in the size range between about 400–5,000 daltons.

As indicated above, the size of the polymer must also be such as to allow chain breakdown of the binder in the material, over a preferably three day to six week period in situ. If binder breakdown is too rapid, the implant mass may lose its shape and particles may migrate away from the site before biofixation can occur. If breakdown is too slow, the binder may inhibit tissue ingrowth, although this problem can be overcome by leaving voids in the implant, as considered below. Studies conducted in support of the present invention indicate that a PLA molecular weight of at least about 400 is desirable to maintain the integrity of implant material during biofixation.

It has not been recognized heretofore that rigid, hard plastics such as PLA and PLA copolymers can form an easily moldable mixture with particulates such as hydroxylapatite at, or slightly above, body temperature. For example, PLA (Tune, D.C., et al, "Evaluation of a High Molecular Weight Polylactide Osteosynthesis Device", Transactions of the Society of Biomaterial, VIII, p 214, 1985) and PLA copolymers (Vert, M., et at, "Stereoregular Bioresorbable Polyester for Orthopaedic Surgery", Makromol Chem Suppl, 5:30–41, 1981) reported in the literature are considered "structural" plastics where advantage is taken of their high mechanical strength, high rigidity coupled with biocompatibility. Surprisingly, by synthesizing the very low molecular weight materials described herein, one can retain the desirable biocompatibility characteristics of polymers such as PLA, while drastically altering their physical properties to produce them in a soft, gummy state that acts as excellent thermosensitive binders for the bone graft material of the present invention.

It is important to recognize that the polymeric binders described here do not rely on chemical reactions to produce a rigid mass as is commonly done with thermosetting polymers such as polymethylmethacrylate (PMMA). Thermosetting polymers generally require initiators to catalyze hardening and such reactions are exothermic. Where PMMA is used, it can generate enough heat to damage adjacent tissue. Thermoset polymers also contain residual unpolymerized monomer which along with catalyst residue give material of questionable and variable biocompatibility. The moldability of thermoset binders is time dependent and not reversible, or reformable once hardened, as is possible for thermoplastics binders.

Once a molecular size range is determined that results in a polymer with desired physical properties, an implant material containing the polymer is tested for stability under conditions of biodegradation. If biodegradation is found to be too rapid, the polymer may be modified, in subunit composition or size, to increase implant stability, or mixed with a slower degrading polymer, such as polylactic acid, to decrease overall binder breakdown rate.

The following example illustrates how a suitable binder polymer is prepared. Lactic acid polymers (polymers of either dl-lactic acid or L(+)-lactic acid) can be prepared by polymerizing the corresponding lactic acid cyclic diester, or lactide, in the presence of a suitable catalyst, such as zinc oxide or boron trifluoride etherate (BTE). In the present example, L(+) lactide, polymeration grade, was obtained from PURAC Inc. (Arlington Heights, IL). The lactide was mixed with a catalyst complex composed of L(+)-lactic acid/BTE, at a mole ratio of between 10 and 100 moles lactide per mole BTE and between 3-15 moles lactide per mole lactic acid. The reactants were heated in an atmosphere of dry nitrogen gas at 100° C. At increasing time intervals up to 24 hours, samples of the mixture were monitored for fluid-flow properties at room temperature. The sample formed after 18-24 hours heating was a transparent semi-solid at room temperature. The molecular-weight of the polymer, determined by gel permeation chromatrography, was in the 400 to 2,000 dalton range.

By similar methods, PLA having progressively greater molecular weights between about 2,000 and 5,000 daltons were prepared and tested for binder characteristics when formulated with hydroxylapatite particles. Above about 2,000 daltons, the implant material was quite hard and difficult to mold by hand at 40° C., and at 5,000 daltons, temperatures up to about 60° C. were reqired to achieve moldability.

To form the implant material of the invention, the binder from above is mixed with hydroxylapatite particles, and the components are thoroughly blended. Preferably the material contains some void space, to allow tissue ingrowth independent of polymer breakdown. Since the void space of a mass of spherical particles is about one-third that of the particle mass, the implant material preferably contains less than about one-third by volume of binder. To optimize the void space, the minimum amount of binder needed to produce good particle cohesiveness, typically between about 5% and 20% of the total solid volume of the material, is added. In one embodiment, implant material containing 80% hydroxylapatite particles (average particle size of about 650 microns), and 20% of PLA polymer having average polymer molecular weights of about 1,100 daltons was prepared. The material was easily moldable by hand at 50° C., and showed good cohesiveness and shape retention at 37° C.

The bone-implant material may be presterilized by heat, gamma radiation, ethylene oxide, or other available methods. For dispensing, the material can be supplied in a syringe or a squeeze-bottle container, allowing direct application of the material into the bone site. Alternatively, the material can be supplied in dish, or flexible roll or block form.

2. Bone Implant Method

The invention includes a method for forming a rigid contour-fitting hard filler implant in a bone site. The method is generally applicable to bone reconstruction or repair needs where a hydroxylapatite or other hard filler bone implant can strengthen a bone region and/or act to transmit stresses to surrounding bone area, to preserve the vitality of bone. Typical applications includes replacing damaged or resorbed bone regions, repairing bone fractures, and filling tooth-extraction sites to help preserve underlying alveolar bone. In addition, the method may be used in anchoring a joint-replacement prosthetic device within a suitable bone cavity.

The bone site which is to receive the implant is prepared by conventional surgical techniques. These usually involve exposing and cleaning the bone site, and may require surgical removal of parts of the bone, for example, to form undercuts at the bone site or to shape the site for more favorable implant seating or stress transmission. For attaching a prosthesis which is designed to be anchored to the bone through a stem, the bone is prepared with a suitable stem-receiving cavity. Here the space between the bone cavity and the prosthesis stem forms the bone site which is to be filled with the implant material.

In practicing the invention, there is provided a moldable hydroxylapatite bone-implant material of the type detailed in Section 1. As described above, implant material having a range of molding temperatures and biodegradability can be provided, by adjusting the composition and amount of binder in the material. Material having a relatively high molding temperature, e.g., between about 40°–60° C., is generally preferred where the implant needs to be in a relatively rigid condition during the process of tissue ingrowth, for example, to prevent significant shape deformation. Here the material is applied and shaped to the bone site in a heated state; after cooling, it assumes the desired rigid condition.

Also as discussed in Section 1 above, the composition and amount of binder can be adjusted to allow for effective tissue ingrowth in the implant material. For example, if the polymer is expected to be degraded only slowly at the bone site, due to lack of enzymes and/or too high a polymer molecular weight, it may be advantageous to provide increased void spaces in the material, by reducing the amount of binder. Similarly, where rapid binder breakdown is expected, a greater amount of binder would be indicated.

The material provided, if its molding temperature is above room temperature, is heated—for example, in hot water or by hot air—until the material is readily moldable by hand. To preserve sterility, the material is preferably heated in a presterilized container, such as a squeeze-bottle container, and applied directly from the container to the site.

To form the implant, the moldable implant material is applied to the bone site to fill the site in a preferably space-filling manner, producing a contour fit between the bone and implant. For the usual bone reconstruction and repair, the material is applied to the bone surface and pressed into or onto the site to force the material into any surface irregularities of the site, such as cracks, holes, and particularly undercut features. The outer surface of the material is then fashioned to give the bone site the desired surface appearance. The latter process may require filling the site with additional material and/or cutting away originally applied material.

In applying the method to prosthesis attachment, the molded material is applied to the outer surface of the prosthesis stem and/or to the inner surface of the bone cavity, in an amount calculated to fill the space between bone and cavity. The stem is then forced into the cavity until the prosthesis is fully seated in the cavity and the implant material is forced substantially completely into the stem/bone space. Where the stem is relatively long, as is the case with the usual femural-side hip-joint replacement prostheses, it is generally advantageous to form a biological bond between bone and stem only in the proximal region of the stem. In this situation, the bone site to be filled with the implant material would be confined to the proximal stem/bone space.

The method of the invention is effective to produce a rigid, contour-fitting implant at the bone site. Unlike solid implants which have been used heretofore, implant rigidity is produced by tissue ingrowth and replacement of binder, and the binder itself only provides initial cohesiveness and semi-rigidity. As mentioned above, the tissue ingrowth typically occurs over about a three-day to six-week period, and can involve tissue ingrowth into the void spaces of the material as well as biodegradation of the binder.

From the foregoing, it can be appreicated how various objects of the invention are met. The implant material is easily applied in moldable form to a bone site, to provide a contour-fitting implant. The method of filling the bone implant with the moldable material avoids the problems of measuring and shaping a rigid-block implant, leads to a better fit than can be achieved with solid implants, and can take advantage of undercut surfaces within the bone site.

At the same time, the material is sufficiently cohesive to resist particle exfoliation during the tissue ingrowth period, and can be made relatively rigid, after cooling, to maintain its contoured shape until it can be rigidified by tissue ingrowth. Through these advantages, the material substantially overcomes problems associated with loose-particle implants.

The material can be formulated with thermoplastic polymer binders of various composition and molecular weights, to achieve a selected molding temperature, rigidity in the bone site, and rate of binder breakdown. By varying the relative proportions of binder and particles, selected changes in the void space and cohesiveness of the material are possible.

While particular embodiments of the invention have been described, it will be appreciated that a variety of changes and modifications can be made without departing from the invention. In particular, it will be readily appreciated by those in the art how polymers of different subunit compositions can be formulated to produce binders having the moldability and breakdown properties described.

It is claimed:

1. A moldable bone-implant material comprising a cohesive mixture of hard filler particles and a biocompatible, biodegradable thermoplastic polymeric binder having fluid-flow properties at or below about 60° C.

2. The material of claim 1, wherein particles are hydroxylapatite.

3. The material of claim 1, wherein the binder constitutes less than about one-third of the material's total volume.

4. The material of claim 1, wherein the binder is biodegradable to normal biochemical metabolite(s).

5. The material of claim 4, wherein the polymer is biodegradable over a period of about three days to six weeks, with the material operatively placed in a bone site.

6. The material of claim 4, wherein the binder is selected from the group consisting of polylactic acid, polyglycolic acid, polyhydroxybutyric acid, polymalic acid, polyglutamine acid, and polylactone.

7. The material of claim 6, wherein the polymer includes polylactic acid having molecular weights between about 400 and 5,000 daltons.

8. The material of claim 7, which is moldable by hand at a selected temperature at or below about 37° C., and the polylactic acid is in the molecular weight range between about 400 and 2,000 daltons.

9. The material of claim 7, which is moldable by hand at a selected temperature above about 40° C., and substantially rigid below about 37° C., and the polylactic acid is in the molecular weight range between about 2,000 and 5,000 daltons.

10. A moldable bone-implant material comprising
    between about 65%–95% hydroxylapatite particles; and
    a binder composed of between about 35%–5% of a polylactic acid polymer having a molecular weight between about 400 and 5,000 daltons.

11. A method of filling a bone site with a contour-fitting, rigid-particle bone implant, comprising
    providing hard filler particles in the form of a moldable bone-implant material composed of a cohesive mixture of the particles and a biocompatible, biodegradable, thermoplastic polymer binder which has fluid-flow properties at a selected temperature at or below about 60° C.,
    heating the material to a temperature which allows the material to be molded by hand, and
    filling the bone site with the moldable material to form a contour-fitting implant at the site,
    where gradual biodegradation of the binder and concomitant ingrowth of surrounding tissue acts to rigidify the implant over a period of several weeks.

12. The method of claim 11, wherein the binder is formed of a polymer having molecular chain sizes which produce such fluid-flow properties at the selected temperature, and
    allow gradual polymer biodegradation over about three days to six weeks, with the material in the bone site.

13. The method of claim 12, wherein the binder is formed by synthesizing the polymer and terminating polymerization when the polymer exhibits such fluid-flow properties at the selected temperature.

14. The method of claim 13, wherein the binder is formed by polymerizing a lactide to form polylactic acid under conditions which lead to polymers in the molecular weight range between about 400–5,000 daltons.

15. The method of claim 11, wherein said providing includes mixing hydroxylapatite particles with no more than about one-third volume of binder.

16. The method of claim 11, wherein the material becomes moldable only above a temperature of about 40° C., and following said filling, the material cools to form a relatively rigid implant.

* * * * *